United States Patent [19]

Sarrell

[11] 4,378,791

[45] Apr. 5, 1983

[54] THERAPEUTIC TRACTION APPARATUS

[75] Inventor: Ivan D. Sarrell, Rising Fawn, Ga.

[73] Assignee: Chattanooga Corporation, Chattanooga, Tenn.

[21] Appl. No.: 184,381

[22] Filed: Sep. 5, 1980

[51] Int. Cl.³ .................... A61F 5/00

[52] U.S. Cl. .................... 128/71

[58] Field of Search .................... 128/76, 72, 71, 84 R, 128/76 R, 78; 73/160

[56] References Cited

U.S. PATENT DOCUMENTS

| | | | |
|---|---|---|---|
| 2,910,061 | 10/1959 | Rabjohn . | |
| 2,940,308 | 6/1960 | Calhoun . | |
| 2,940,442 | 6/1960 | Wilhelm . | |
| 3,085,768 | 4/1963 | Treutelaar . | |
| 3,086,518 | 4/1963 | Barlow et al. . | |
| 3,117,572 | 1/1964 | Wright . | |
| 3,168,094 | 2/1965 | Siltamaki . | |
| 3,710,787 | 1/1973 | Rabjohn . | |
| 3,786,803 | 1/1974 | Petulla et al. . | |
| 3,831,444 | 8/1974 | Sasaki | 73/160 |
| 3,835,847 | 9/1974 | Smith . | |
| 3,937,216 | 2/1976 | Brown . | |
| 3,952,235 | 4/1976 | Peters . | |
| 4,097,037 | 6/1978 | Tardiff . | |
| 4,258,707 | 3/1981 | Lettinga | 128/75 |
| 4,266,537 | 5/1981 | Bonin | 128/75 |

FOREIGN PATENT DOCUMENTS

| | | | |
|---|---|---|---|
| 2001185 | 7/1978 | United Kingdom . | |
| 197711 | 11/1977 | U.S.S.R. | 128/75 |

*Primary Examiner*—Richard J. Apley
*Assistant Examiner*—George Yanulis
*Attorney, Agent, or Firm*—Bell, Seltzer, Park & Gibson

[57] ABSTRACT

An apparatus is disclosed which is adapted to statically or intermittently apply a traction force to the body of a patient for therapeutic purposes. The apparatus includes a novel control means for cyclically reversing the direction of rotation of the wind-up drum upon predetermined minimum and maximum forces being present in the tension cord, and wherein the actual tension in the cord is monitored by a control circuit which provides an electrical output which is linearly porportional to the tension. The output signal is fed to a comparator circuit, where it is compared with independently selectable signals representing minimum and maximum tension forces, to control the wind-up and wind-down of the cord on the drum. The apparatus further includes several safety features for assuring the proper and safe functioning of the apparatus.

13 Claims, 7 Drawing Figures

THERAPEUTIC TRACTION APPARATUS

The present invention relates to an improved therapeutic apparatus adapted for statically or intermittently applying a traction force to the body of a patient.

Traction forces have long been utilized in the physical therapy field for the treatment of various orthopedic disorders, muscular conditions, and the like. Originally, the traction was applied statically using a system of weights, but more recently a number of powered devices have been developed for applying the traction force intermittently, which permits a greater force to be applied without undue patient discomfort.

In one presently commercialized traction apparatus of this type, a pneumatically actuated piston assembly is provided for applying a pulling force to one end of a cord, with the other end of the cord being adapted for attachment to an appliance worn by the patient. The applied force is monitored by a pressure transducer, which in turn acts to cyclically reverse the pulling force of the piston assembly upon predetermined maximum and minimum forces being applied. Electronic controls are also provided for selectively operating in one of four treatment modes, namely, a static mode wherein the preselected maximum force is held throughout the treatment period, a progressive static mode wherein the force is initially applied in a number of increasing steps until the preselected maximum force is reached, with the maximum force then being held for the remaining treatment time, an intermittent mode wherein the force is cyclically applied between preselected minimum and maximum levels, and a progressive intermittent mode wherein the upper force level progressively increases during the initial cycles and until the desired maximum force is obtained. While this pneumatically operated apparatus has achieved a high degree of commercial acceptance, the pneumatic components are necessarily somewhat bulky in physical size, which limits the utility of the apparatus for use with certain types of support stands or treatment tables.

Another traction apparatus which is adapted for operation in a number of different treatment modes is disclosed in published United Kingdom patent application No. GB 2001185. This apparatus is electrically powered, and includes a drum having a traction cord wound thereon, an electric motor for selectively rotating the drum in either direction, a pair of individual control slides mounting limit switches for selecting the desired maximum and minimum forces, and a mechanical assembly for actuating the limit switches upon the preselected forces being reached to thereby reverse the direction of motor rotation and thus provide intermittent operation. It is apparent however that the mechanical force sensing assembly as disclosed in this U.K. application is not linearly responsive to the actual force in the cord, by reason of the angular disposition of the traction cord through the sensing assembly, and thus a non-linear read-out scale for the control slides would be required on the control panel, which would complicate the design and appearance of the scales. Also, it is believed that the mechanical nature of the disclosed slides and limit switches would not be able to provide a high degree of accuracy and reliability in the operation of the apparatus.

It is accordingly an object of the present invention to provide a therapeutic traction applying apparatus adapted for intermittent operation, and having a compact, highly accurate and reliable control system for monitoring the actual tension in the cord and effecting cyclical reversal of the drive motor upon predetermined maximum and minimum forces being present in the cord.

It is a further and more particular object of the present invention to provide an intermittent traction applying apparatus of the type wherein the traction cord is wound upon a powered drum, and wherein the control system for monitoring the actual tension provides a continuous output which is linearly representative of the actual tension in the cord, to thereby greatly simplify the design of the control system and associated read-out scales.

It is a further object of the present invention to provide an intermittent traction apparatus of the described type, and wherein the tension monitoring control system and the variable maximum and minimum force level controls are essentially electronic, to provide a high degree of accuracy and reliability in the operation of the apparatus, and which further incorporates a relatively large number of readily selectable operational modes, as well as a number of electronic circuits for continuously monitoring the proper and safe operation of the apparatus.

These and other objects and advantages of the present invention are achieved in the embodiment illustrated herein by the provision of a therapeutic traction apparatus having an electrically powered drum, a traction cord wound upon the drum, and control means for cyclically reversing the direction of rotation of the drum and which includes means for generating an electrical output signal (Eo) which is linearly proportional to the actual tension in the cord. Further, first force controlling means is provided for generating an electrical output signal (Emax) representing a desired maximum tension in the cord, a second force controlling means is provided for generating an electrical output signal (Emin) representing a desired minimum tension in the cord, and comparator circuit means is provided for cyclically connecting the motor for rotation of the drum in the wind-up direction upon Eo equaling or being less than Emin, and connecting the motor for rotation of the drum in the winddown direction upon Eo equalling or exceeding Emax.

In the preferred embodiment, the means for generating an electrical output signal which is linearly proportional to the tension in the cord includes a pair of first and second cord guides mounted a fixed distance apart from each other, a third cord guide mounted for movement toward the pair of guides along a direction which perpendicularly bisects the distance between the pair of guides, and with the cord being disposed along a generally U-shaped path of travel which contacts each of the pair of guides and extends around the third guide so as to define two substantially parallel runs of the cord, and such that tension in the cord tends to move the third guide toward the pair of guides. A spring is provided for applying a biasing force which resists displacement of the third guide toward the pair of guides, with the resisting force thereof being substantially linearly proportional to the amount of such displacement. Means including a linear transducer are further provided for detecting such displacement and providing an electrical output signal which is proportional thereto.

Some of the objects having been stated, other objects will appear as the description proceeds, when taken in connection with the accompanying drawings, in which FIG. 1 is a perspective view of an intermittent traction applying apparatus embodying the present invention, and mounted on a conventional traction table;

Figure 1:
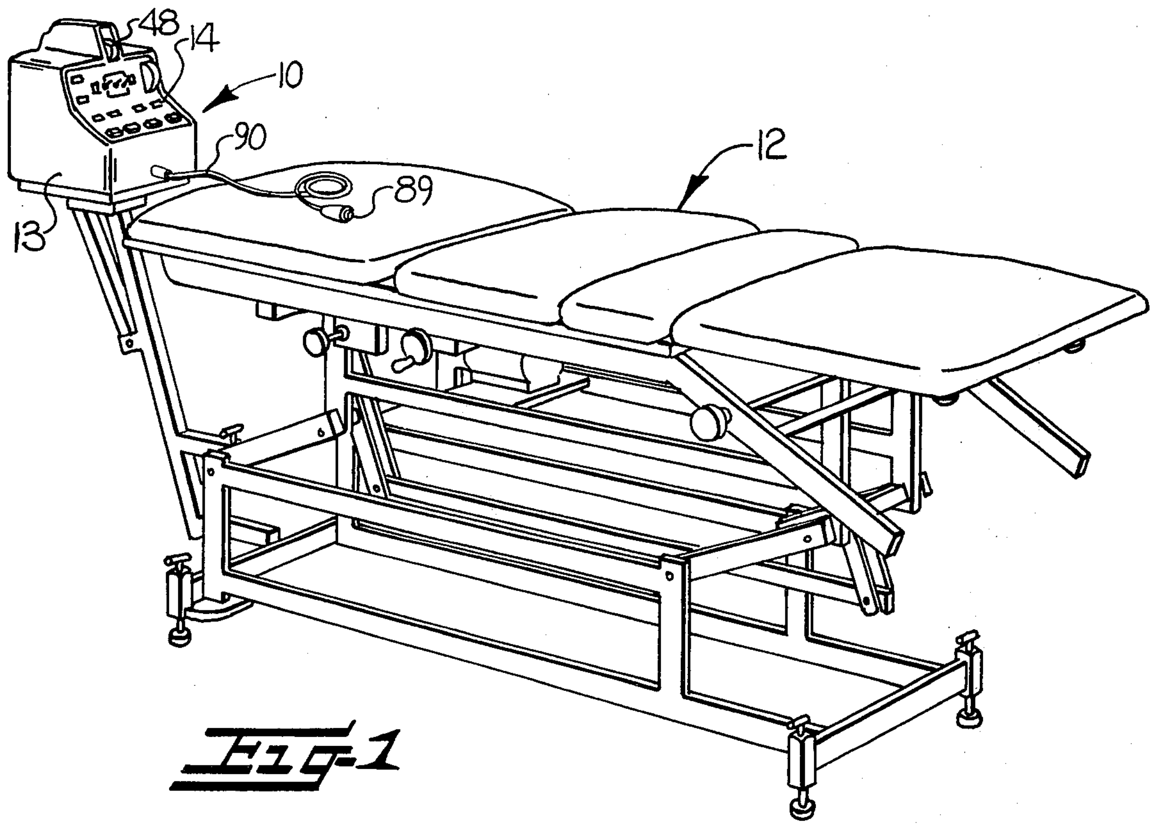

Referring more specifically to the drawings, a traction applying apparatus in accordance with the present invention is illustrated generally at 10 in FIG. 1, with the apparatus being shown affixed in an operative position to one end of a conventional traction table 12. As illustrated, the apparatus 10 includes a box-like housing 13 which contains the various components and controls of the apparatus as further described below, with these components and controls being illustrated in somewhat schematic fashion in the drawings in order to facilitate the understanding of the invention.

Figure 3:
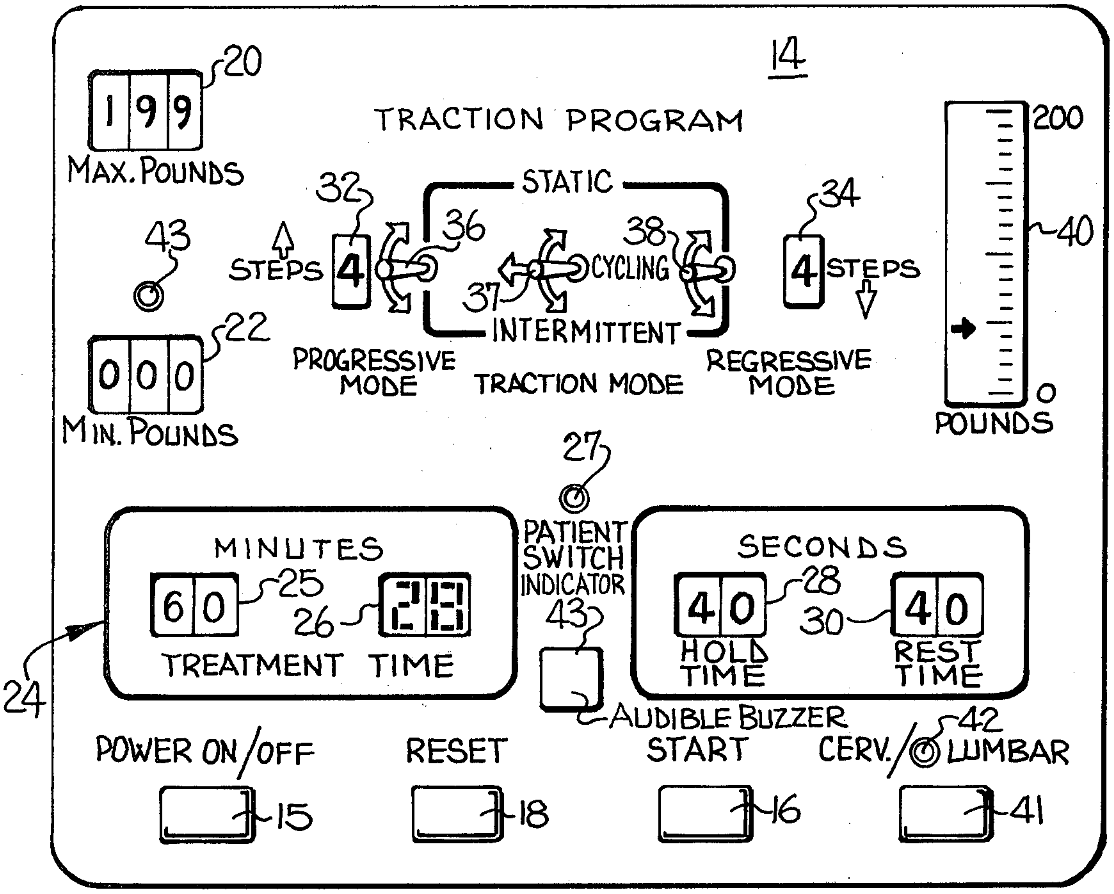
FIG. 3 is a front elevation view of the control panel on the traction applying apparatus illustrated in FIG. 1.

As seen in FIG. 3, the apparatus 10 includes a front control panel 14 which conveniently mounts the various manual controls and read-outs utilized in the operation of the apparatus, and as further described below. Generally described, the panel 14 mounts a master on-off switch 15 which controls the electric power to the apparatus, a start switch 16 which sets the apparatus into operation, and a reset switch 18 which acts to stop treatment or return treatment to zero traction. The panel also mounts a manually adjustable maximum tension dial 20 with digital readout, a manually adjustable minimum tension dial 22 with a similar readout, a master timer 24 having a manually adjustable dial 25 with digital readout and a separate digital read-out display 26 of the time remaining in the total treatment time, a patient control switch indicator 27, an adjustable hold timer dial and readout 28, an adjustable rest timer dial and readout 30, an adjustable step-up dial and readout 32, an adjustable step-down dial and readout 34, and three switches 36, 37, 38 for selecting one of the modes of operation as further described below. The panel further mounts a meter 40 adapted to display the actual tension in the cord, an illuminated cervical-lumbar safety switch 41, which flashes on and off when in lumbar mode, and an associated indicator light 42, a further indicator light 43 for indicating an improper setting of the maximum and minimum tension dials 20 and 22, and an audible alarm buzzer 44.

Figure 2:
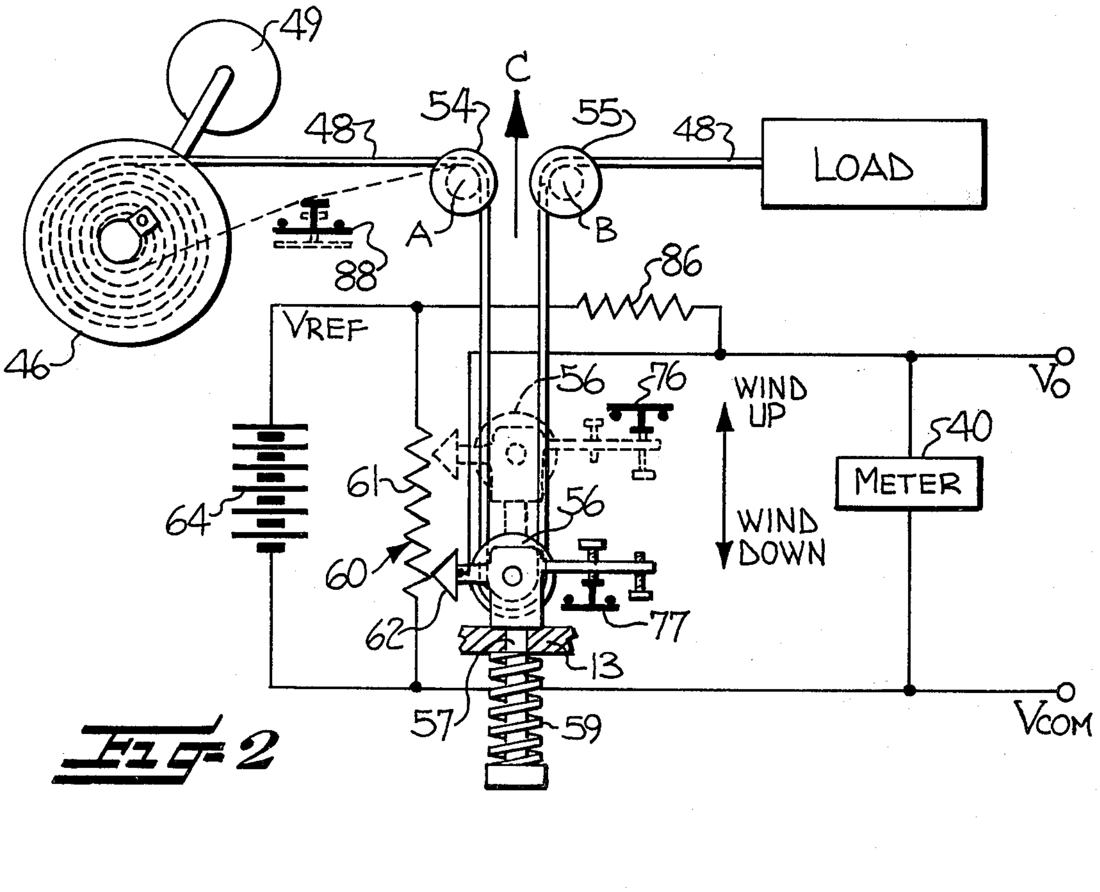
FIG. 2 is a schematic representation of the means incorporated in the traction applying apparatus for generating an electrical output signal which is linearly proportional to the tension in the cord.

As seen in FIG. 2, the housing rotatably mounts a drum 46, which has one end of a traction cord 48 wound thereupon, and with the other end of the cord extending from the housing 13 and being adapted to be affixed to a traction appliance or load. A reversible electrical motor 49 is provided for rotating the drum in either direction by the selective closing of either the wind-up switch 50 (FIG. 4) or the wind-down switch 51 to thereby selectively wind-up or wind-down the cord on the drum.

There is further provided control means in the housing for cyclically reversing the direction of rotation of the drum 46 upon predetermined minimum and maximum forces being present in the cord. In accordance with the present invention, this control means includes means for continuously monitoring the tension in the cord 48 and for generating an electrical output signal (Eo) which is linearly proportional to such tension. This monitoring and generating means comprises a pair of first and second cord guides or pulleys 54, 55 mounted a fixed distance apart from each other and defining a first direction extending therebetween, i.e. the direction between points A and B in FIG. 2. A third cord guide or pulley 56 is rotatably mounted on a post 57, which is mounted for linear movement in the housing 13, and such that the third pulley 56 moves along a second direction indicated by the arrow C which is perpendicular to the direction A-B and bisects the distance between the pulleys 54 and 55. The traction cord 48 is disposed along a generally U-shaped path of travel so as to contact each of the fixed pulleys 54, 55 and extend around the movable pulley 56 to define two substantially parallel runs of the cord, and such that tension in the cord tends to move the pulley 56 toward the fixed pulleys 54, 55 along the second direction C to shorten the distance therebetween.

The post 57 of the third pulley 56 mounts a coil spring 59 for applying a biasing force which resists movement of the third pulley toward the pair of pulleys caused by tension in the cord. By choice in the design of the spring 59, the resisting force is substantially linearly proportional to the amount of the deflection of the third pulley from a preselected maximum distance as shown in solid lines in FIG. 2, to a point of maximum tension and deflection as indicated by the dashed line position of the pulley 56 in FIG. 2.

In order to detect the deflection of the third pulley 56 toward the pair of fixed pulleys 54, 55 and for providing an electrical output signal which is proportional to such deflection, there is further provided a control transducer in the form of a linear potentiometer 60, which includes a resistance component 61, and a wiper 62 which is fixed to the third pulley 56 so as to move along the resistance component 61. Linear potentiometers of this type, and which are designed to produce an output proportional to the deflection of the wiper along its resistive component, are per se well known in the art. A voltage source 64 provides a control voltage across the resistive component 61, and the output of the potentiometer (Eo) is obtained across the lines Vo and Vcom. The output of the potentiometer 60 is also operatively connected to the meter 40, which provides a visual display of the actual tension in the cord on the front panel 14. As will be apparent to those skilled in the art, other types of transducers for linearly transducing the deflection to an electrical output could be employed with the present invention, such as a capacitive, electromagnetic, or photoelectric linear transducer.

The control means of the present invention further comprises first force controlling means for generating an electrical output signal (Emax) representing a desired maximum tension in the cord. In the illustrated embodiment, this first force controlling means includes the manually adjustable dial 20 mounted on the front panel of the housing for selecting the maximum force and providing a visual read-out of the same. Typically, the apparatus is designed such that the maximum force cannot exceed 200 pounds. The dial 20 is operatively connected to a transducer, which as illustrated comprises the potentiometer 66 (FIG. 6) having a resistance component 67 and a wiper 68. The control means further includes a second force controlling means for generating an electrical output signal (Emin) representing a desired minimum tension in the cord. This second force controlling means includes the manually adjustable dial t22 mounted on the front panel, and an associated transducer, which as illustrated comprises the potentiometer 70 which has a resistive component 71 and wiper 72.

Figure 6:
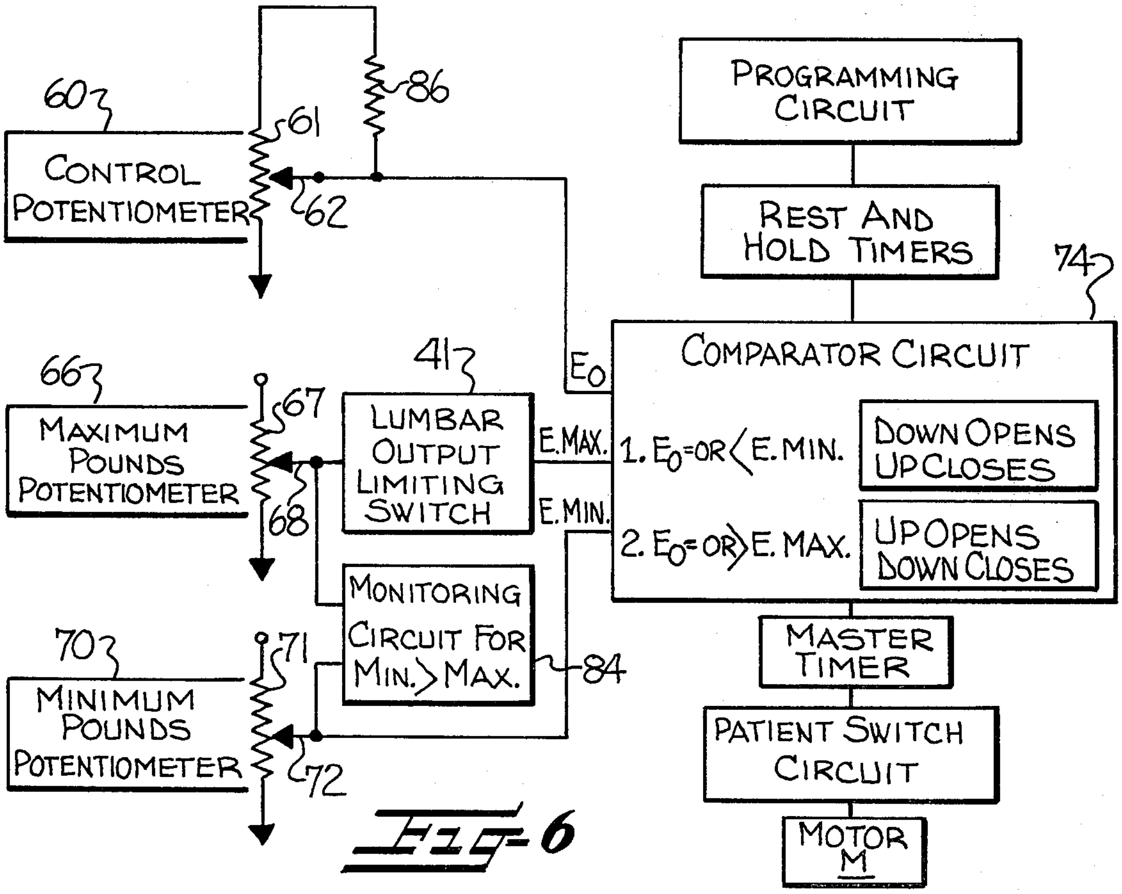
FIG. 6 is a schematic representation of the control circuitry utilized with the apparatus of the present invention.

The outputs of the three potentiometers 60, 66 and 70 are directed to a comparator circuit as shown schematically at 74 in FIG. 6, the operation of which is controlled by the particular programming circuit selected by the operator. In each case however, the comparator circuit continuously compares Eo with Emin and Emax, and functions to open the wind-down switch 51 and close the wind-up switch 50 to electrically connect the motor 49 for rotation of the drum 46 in the wind-up direction upon Eo equaling or being less than Emin, and to open the wind-up switch 50 and close the wind-down switch 51 to connect the motor for rotation of the drum in the wind-down direction upon Eo equaling or exceeding Emax.

Figure 7:
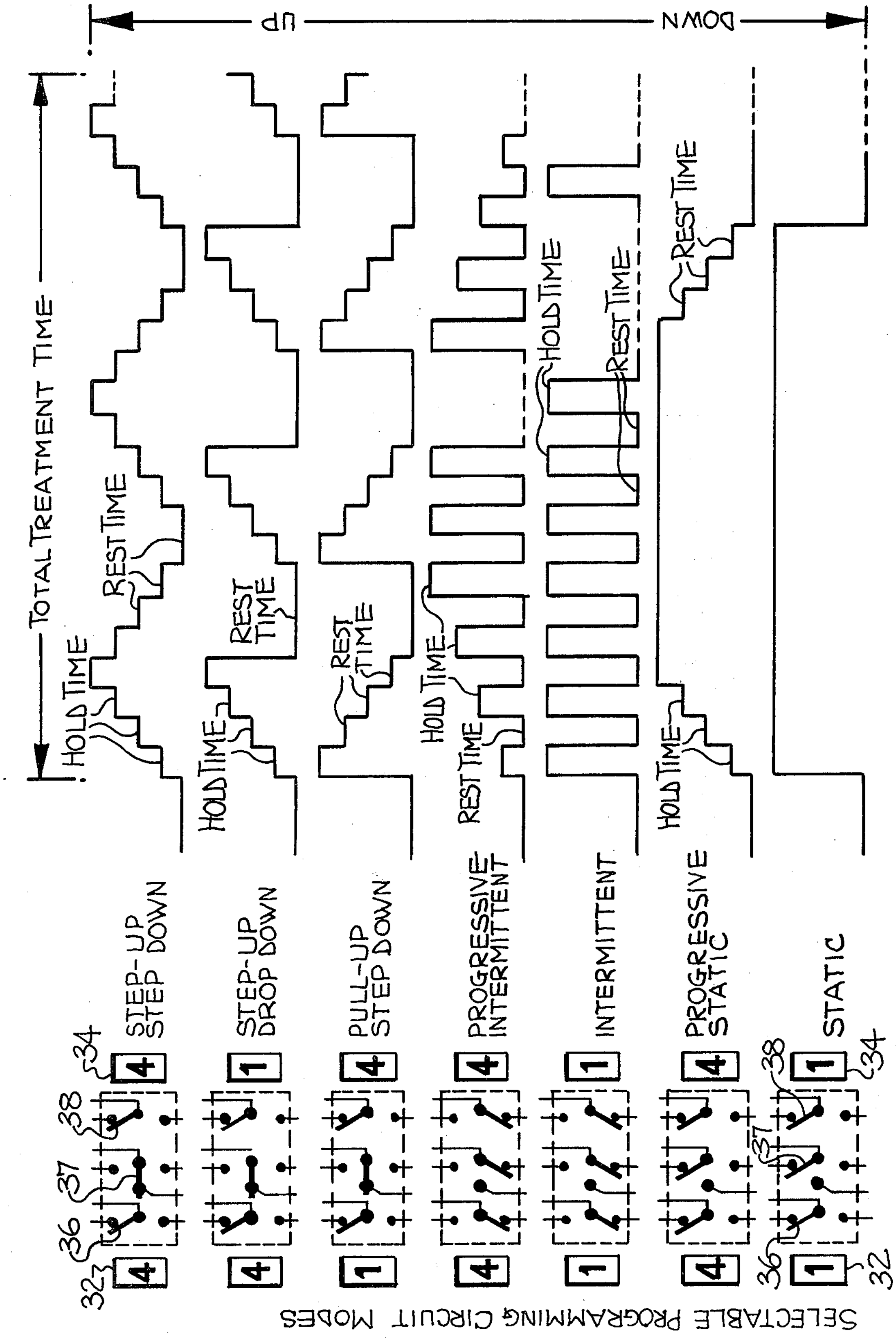
FIG. 7 is a schematic representation of the several selectable modes of operation of the apparatus of the present invention.

The illustrated embodiment of the apparatus includes a programming circuit having seven selectable modes of operation as illustrated schematically in FIG. 7. The particular mode is determined by the setting of the three switches 36, 37, 38 on the front panel of the apparatus in the manner also indicated in FIG. 7. Also, the selectable programming circuit modes include provision for sequentially operating the rotation of the drum so as to increase the tension in a selected number of progressive steps, and the step-up selector dial 32 on the front panel permits the number of progressive steps to be selectively chosen. Typically, the apparatus is designed to permit the dial 32 to choose from one to nine progressive steps. Similarly, the programming circuit modes include provision for sequentially operating the rotation of the drum so as to decrease the tension in a selected number of regressive steps, with the number of such steps being determined by the step-down selector dial 34 on the front panel. Thus for example, in the cycling step-up step-down mode as illustrated in FIG. 7, the programming circuit operates to sequentially rotate the drum so as to increase the tension in four progressive steps as determined by the setting of the dial 32, and to sequentially rotate the drum so as to decrease the tension in four regressive steps as determined by the setting of the dial 34. The hold timer 28 acts to hold the force at each of the progressive steps for the selected time (typically 1 to 60 seconds) as indicated in FIG. 7, and the rest timer 30 acts to hold the force at each of the regressive steps for the selected time in the manner illustrated in FIG. 7. In the progressive intermittent mode, Emax is sequentially increased for a predetermined number of cycles as determined by the setting of the dial 32, then held at a fixed level for a number of cycles determined by the total treatment time set by the master timer 24, and then sequentially decreased for a predetermined number of cycles determined by the setting of the dial 34.

Figure 4:
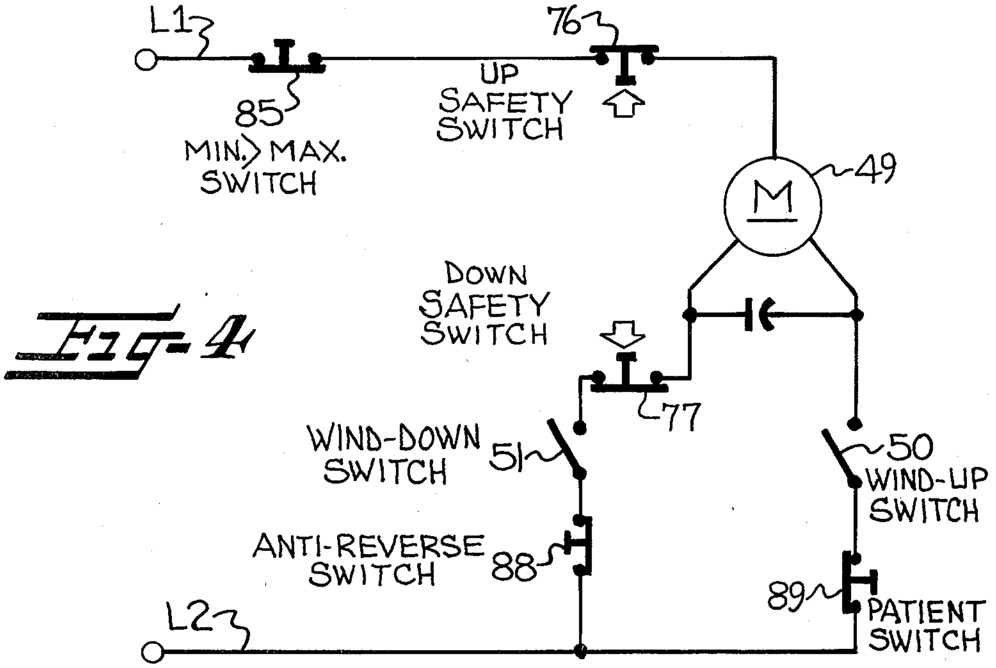
FIG. 4 is a schematic representation of the motor control circuit for the apparatus of the present invention.

In order to prevent the overrun of the third pulley 56 past the maximum safe tension level, i.e. 200 pounds, there is provided an overrun safety switch 76, as best seen in FIGS. 2 and 4. The up safety switch 76 is opened upon the distance between the pulley 56 and pair of pulleys 54, 55 being less than a predetermined minimum distance which represents the maximum permissible tension, and the opening of the switch 76 acts to open the drive motor circuit. Similarly, the down safety switch 77 is opened upon the distance between the pulley 56 and the pair of pulleys 54, 55 equaling a maximum distance which represents zero tension, to thereby open the down motor line. As will be understood, the overrun safety switches 76, 77 are not normally actuated, since the setting of the maximum and minimum potentiometers 66 and 70 will reverse the motor prior to the overrun switches being actuated.

Figure 5:
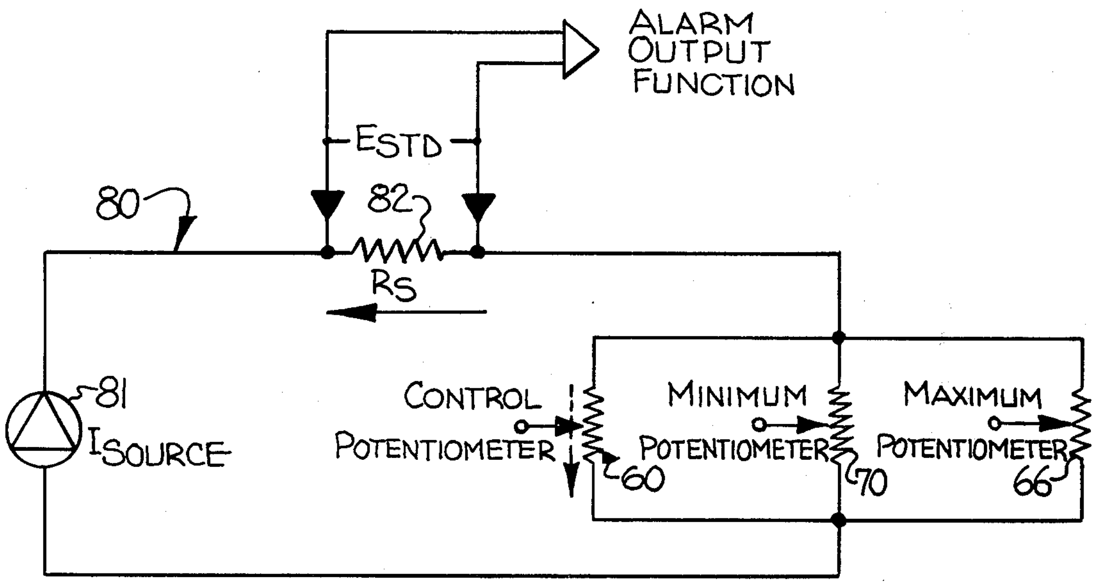
FIG. 5 is a schematic representation of the monitoring circuit for detecting the failure of the resistance component of each of the three transducers utilized in the apparatus of the present invention.

FIG. 5 illustrates a monitoring circuit 80 for detecting a failure or short in the resistance component of each of the three potentiometers 60, 66, 70 and for generating an output signal upon such failure being detected which is operable to cause wind-down of the motor and actuate the alarm buzzer 44. Thus for example, if the resistance component 61 of the control potentiometer shorted to ground or opened above the wiper 62 as seen in FIG. 6, there would be no output and the motor would tend to continue winding up until the up safety switch 76 was opened. Similarly, if the resistance component 67 of the maximum potentiometer opened below the wiper 68 as seen in FIG. 6, the motor would tend to continue to wind-up the cord until the up safety switch was opened. Thus the monitoring circuit 80 and the up safety switch 76 provide redundant protection against the application of a dangerously high traction force.

The monitoring circuit 80 mounts the three potentiometers in parallel, and the circuit includes a current source 81 for applying a predetermined voltage across the three potentiometers, and a standard resistance 82. The voltage across the standard resistance 82 is monitored, such that a change caused by the failure of one of the three potentiometers causes the alarm circuit to be actuated, and the motor wind-down switch 51 to close.

It will be apparent that should the minimum tension dial 22 be inadvertently set at a tension level higher than that of the maximum tension dial 20, the apparatus would improperly operate. To avoid this possibility, there is provided a further monitoring circuit 84 (FIG. 6) which compares the setting of the maximum tension dial 20 with the setting of the minimum tension dial 22, and acts to open the switch 85 (FIG. 2) and thereby preclude operation of the motor 49 upon the setting of the minimum dial 22 exceeding that of the maximum dial 20. An improper setting also causes the warning light 43 to be illuminated on the front panel.

In the event of an open circuit between the resistance component 61 and wiper 62 of the control potentiometer 60, a zero output would be obtained which would cause the motor 49 to continue to wind-up, until the up safety switch 76 is opened. To preclude this possibility, there is provided a wiper verification circuit which includes a resistance 86 positioned in parallel across the resistance component 61 and the wiper 62 of the potentiometer 60. Thus in the event of an open circuit, the current passes through the resistance 86, which is designed to provide an output equivalent to that produced by the potentiometer 60 at its maximum tension setting, to thereby cause the motor 49 to run in the wind-down direction and then cease operation.

The cervical-lumbar switch 41 acts to permit the limiting of the maximum output of the control potentiometer 60 to a predetermined level, such that the maximum tension applied by the apparatus may be selected by the actuation of this switch. More particularly, the apparatus is normally operated in the cervical mode, wherein the maximum output is set, for example, at a level of 40 pounds tension. In order to achieve a higher level of tension, the switch 41 must be set in the lumbar mode. Unless switch 41 is actuated, the red warning light 42 will be illuminated, indicating lumbar mode was not properly selected.

Should the apparatus malfunction to continue rotation of the drum 46 in the wind-down direction past the minimum tension level, the cord 48, which has one end fixed to the drum, would totally pay out and then would start to reversely wind upon the drum. Thus tension would be applied with the drum rotating in the wind-down direction. To preclude this possibility, there is provided an anti-reverse switch 88 (FIGS. 2 and 4) mounted adjacent the drum and operable by contact with the cord upon the cord being wound in the reverse direction. The opening of the normally closed anti-reverse switch precludes operation of the motor in the wind-down direction in the manner best seen in FIG. 4.

To permit the patient to terminate application of the traction force, there is provided a patient switch 89, which is mounted at the end of a cord 90 so as to be readily accessible. Actuation of the switch 89 causes the motor 49 to wind-down and cease operation, and the indicator 27 on the front panel to be illuminated.

In the drawings and specification there has been set forth a preferred embodiment of the invention, and although specific terms are employed they are used in a generic and descriptive sense only and not for purposes of limitation.

That which is claimed is:

1. In a therapeutic traction applying apparatus adapted to intermittently apply a traction force to the body of a patient, and comprising a rotatably mounted drum, a length of cord having one end wound upon said drum and an opposite end adapted to be affixed to a traction appliance positioned on a patient, power means for rotating said drum in either direction to thereby selectively either wind-up or wind-down the cord on said drum, and control means for cyclically reversing the direction of rotation of said drum upon predetermined minimum and maximum forces being present in said cord, the improvement wherein said control means comprises means for continuously monitoring the tension in said cord and for generating an electrical output signal (Eo) which is linearly proportional to such tension, first force controlling means for generating an electrical output signal (Emax) representing a desired maximum tension in said cord, second force controlling means for generating an electrical output signal (Emin) representing a desired minimum tension in said cord, and comparator circuit means for cyclically connecting said power means for rotation of said drum in the wind-up direction upon Eo equaling or being less than Emin, and connecting said power means for rotation of said drum in the wind-down direction upon Eo equaling or exceeding Emax.

2. In the therapeutic traction applying apparatus as defined in claim 1 wherein each of said first and second force controlling means is manually adjustable to permit individual adjustment of the tension represented thereby.

3. In a therapeutic traction applying apparatus as defined in claim 2 wherein each of said first and second force controlling means is digitally adjustable.

4. In the therapeutic traction applying apparatus as defined in claim 1 further comprising selectively operable programmed circuit means for sequentially operating the rotation of said drum so as to increase the tension in a selected number of progressive steps, and selector means for varying said selected number of progressive steps.

5. In the therapeutic traction applying apparatus as defined in claim 4 wherein said selectively operable programmed circuit means further includes means for cyclically operating the rotation of said drum so as to decrease the tension in a selected number of regressive steps, and selector means for varying said selected number of regressive steps.

6. In the therapeutic traction applying apparatus as defined in claim 5 wherein said control means further includes manually adjustable hold timer means for holding the tension at each of said progressive steps for a predetermined time, and manually adjustable rest timer means for holding the tension at each of said regressive steps for a predetermined time.

7. In the therapeutic traction applying apparatus as defined in claim 1 further comprising selectively operable programmed circuit means for sequentially increasing Emax for a predetermined number of cycles, then holding Emax at a fixed level for a plurality of cycles, and then sequentially decreasing Emax for a predetermined number of cycles.

8. In the therapeutic traction applying apparatus as defined in claim 1 wherein said means for monitoring the tension in the cord and for generating an electrical output signal (Eo) comprises a pair of first and second cord guides mounted a fixed distance apart from each other and defining a first direction extending therebetween, a third cord guide mounted for movement with respect to said pair of guides along a second direction which is perpendicular to said first direction and bisects the distance between said pair of guides, with said cord being disposed along a path of travel which contacts each of said pair of guides and extends around said third guide so as to define two substantially parallel runs of the cord, and such that tension in said cord tends to move said third guide with respect to said pair of guides along said second direction to shorten the distance therebetween, spring biasing means for applying a force which resists movement of said third guide with respect to said pair of cord guides along said second direction caused by tension in said cord, and with the resisting force being substantially linearly proportional to the amount of such movement, and means for providing an electrical output signal proportional to the amount of such movement.

9. In the therapeutic traction applying apparatus as defined in claim 8 further comprising first safety switch means for terminating operation of said power means upon the distance between said third cord guide and said pair of cord guides being less than a predetermined minimum distance representing the maximum permissible tension.

10. In the therapeutic traction applying apparatus as defined in either claim 8 or 9 further comprising second safety switch means for terminating operation of said power means upon the distance between said third cord guide and said pair of cord guides exceeding a predetermined maximum distance representing the desired minimum tension.

11. In the therapeutic traction applying apparatus as defined in claim 8 wherein said means for providing an electrical output signal proportional to the amount of such movement includes a linear transducer.

12. In the therapeutic traction applying apparatus as defined in claim 10 further comprising a display meter operatively connected to said linear transducer for visually indicating the actual tension in said cord.

13. In the therapeutic traction applying apparatus as defined in claim 1 further comprising anti-reverse switch means mounted adjacent said drum and operable upon the cord being wound thereupon in the reverse direction to preclude operation of said power means and thereby prevent tensioning of said cord by rotation of said drum in the wind-down direction.

* * * * *